(12) United States Patent
Hansen et al.

(10) Patent No.: US 12,017,049 B2
(45) Date of Patent: Jun. 25, 2024

(54) HOUSING FOR A MEDICAL INJECTION DEVICE

(71) Applicant: Novo Nordisk A/S, Bagsvaerd (DK)

(72) Inventors: Ken Hansen, Vejle (DK); Imran Ghulam, Copenhagen SV (DK); Jesper Bach Noergaard, Virum (DK); Claus Urup Gjoedesen, Holte (DK); Asger Meng Larsen, Valby (DK)

(73) Assignee: Novo Nordisk A/S, Bagsvaerd (DK)

( * ) Notice: Subject to any disclaimer, the term of this patent is extended or adjusted under 35 U.S.C. 154(b) by 739 days.

(21) Appl. No.: 17/009,830

(22) Filed: Sep. 2, 2020

(65) Prior Publication Data

US 2020/0397997 A1 Dec. 24, 2020

Related U.S. Application Data

(62) Division of application No. 15/578,326, filed as application No. PCT/EP2016/062039 on May 27, 2016, now Pat. No. 10,799,644.

(30) Foreign Application Priority Data

Jun. 1, 2015 (EP) ..................... 15170130

(51) Int. Cl.
*A61M 5/315* (2006.01)
*A61M 5/20* (2006.01)
(Continued)

(52) U.S. Cl.
CPC ...... *A61M 5/31553* (2013.01); *A61M 5/3129* (2013.01); *A61M 5/31551* (2013.01);
(Continued)

(58) Field of Classification Search
CPC ............ A61M 5/31553; A61M 5/3129; A61M 5/31551; A61M 5/31563; A61M 5/2033
See application file for complete search history.

(56) References Cited

U.S. PATENT DOCUMENTS

| 2,587,147 A | 2/1952 | Guion et al. |
| 3,712,301 A | 1/1973 | Sarnoff |

(Continued)

FOREIGN PATENT DOCUMENTS

| CN | 103442754 A | 12/2013 |
| CN | 103533975 A | 1/2014 |

(Continued)

OTHER PUBLICATIONS

NovoPen® 3 (Insulin Delivery System), Novo Nordisk Pharmaceuticals, Inc., 1998.

(Continued)

*Primary Examiner* — Dung T Ulsh
(74) *Attorney, Agent, or Firm* — Wesley Nicolas

(57) ABSTRACT

The invention relates to a medical injection device having a polymeric housing or housing parts. The housing comprises a moulded outer housing element and a moulded elongated tubular inner housing element. The elongated tubular inner housing element is formed as one unitary element and carries a pointer and one or more projections in predetermined and correlated positions. The pointer points to indicia on a scale drum and the projections engage the scale drum. The outer housing element is moulded over the elongated tubular inner housing element in a 2K moulding to form one single housing component.

10 Claims, 3 Drawing Sheets

(51) Int. Cl.
    *A61M 5/31*     (2006.01)
    *B29C 45/14*     (2006.01)
    *B29C 45/16*     (2006.01)
    *B29L 31/00*     (2006.01)

(52) U.S. Cl.
    CPC ......... *A61M 5/31563* (2013.01); *B29C 45/16* (2013.01); *A61M 5/2033* (2013.01); *A61M 2005/3126* (2013.01); *A61M 2205/583* (2013.01); *A61M 2207/00* (2013.01); *B29C 45/14336* (2013.01); *B29L 2031/7544* (2013.01)

(56) References Cited

U.S. PATENT DOCUMENTS

| | | |
|---|---|---|
| 4,822,340 A | 4/1989 | Kamstra |
| 4,973,318 A * | 11/1990 | Holm .................... A61M 5/24 604/218 |
| 5,295,965 A | 3/1994 | Wilmot |
| 6,171,283 B1 | 1/2001 | Perez et al. |
| 6,454,746 B1 | 9/2002 | Bydlon et al. |
| 6,682,504 B2 | 1/2004 | Nelson et al. |
| 7,377,913 B2 | 5/2008 | Gurtner |
| 8,652,387 B2 | 2/2014 | Etter et al. |
| 8,915,887 B2 | 12/2014 | Avlund |
| 9,878,102 B2 | 1/2018 | Julian et al. |
| 9,901,685 B2 | 2/2018 | Pedersen |
| 10,350,358 B2 | 7/2019 | Schenker et al. |
| 10,799,644 B2 | 10/2020 | Hansen et al. |
| 11,241,544 B2 | 2/2022 | Hansen et al. |
| 2004/0254543 A1 | 12/2004 | Griffiths |
| 2005/0241112 A1 | 11/2005 | Worrell |
| 2007/0176322 A1 | 8/2007 | Etter et al. |
| 2010/0152667 A1 | 6/2010 | Kietzmann |
| 2010/0274198 A1 | 10/2010 | Bechtold |
| 2012/0053527 A1 | 3/2012 | Cirillo et al. |
| 2012/0203177 A1 | 8/2012 | Lanier, Jr. et al. |
| 2012/0289905 A1 | 11/2012 | Julian et al. |
| 2012/0300421 A1 | 11/2012 | Askarinya et al. |
| 2015/0018776 A1 * | 1/2015 | Schenker .......... A61M 5/31528 604/207 |
| 2015/0080807 A1 * | 3/2015 | Schneider ........... A61M 5/3155 604/207 |
| 2016/0129196 A1 | 5/2016 | Hirschel et al. |
| 2016/0213855 A1 * | 7/2016 | Marsh ............... A61M 5/31583 |
| 2017/0319793 A1 | 11/2017 | Bergens |
| 2018/0147363 A1 | 5/2018 | Hansen et al. |

FOREIGN PATENT DOCUMENTS

| | | |
|---|---|---|
| CN | 104271185 A | 1/2015 |
| CN | 104349806 A | 2/2015 |
| EP | 1603610 A1 | 12/2005 |
| EP | 1819382 A1 | 8/2007 |
| GB | 706620 A | 3/1954 |
| GB | 2325328 A | 11/1998 |
| JP | 2012000146 A | 1/2012 |
| JP | 6543250 B2 | 7/2019 |
| WO | 9810813 | 3/1998 |
| WO | 9938554 | 8/1999 |
| WO | 9938554 A1 | 8/1999 |
| WO | 00/73040 A1 | 12/2000 |
| WO | 0195959 A1 | 12/2001 |
| WO | 02064199 A1 | 8/2002 |
| WO | 2004064902 A1 | 8/2004 |
| WO | 2004078241 A1 | 9/2004 |
| WO | 2006045528 A1 | 5/2006 |
| WO | 2007067889 A1 | 6/2007 |
| WO | 2007/107431 A1 | 9/2007 |
| WO | 2008128645 A1 | 10/2008 |
| WO | 2008148864 A1 | 12/2008 |
| WO | 2010020311 A1 | 2/2010 |
| WO | 2011082272 A2 | 7/2011 |
| WO | 2012046199 A1 | 4/2012 |
| WO | 2012135524 A1 | 10/2012 |
| WO | 2012143437 A1 | 10/2012 |
| WO | 2013110538 A1 | 8/2013 |
| WO | 2013134486 A2 | 9/2013 |
| WO | 2015/017550 A1 | 2/2015 |
| WO | 2015082303 A1 | 6/2015 |
| WO | 2015/197629 A1 | 12/2015 |

OTHER PUBLICATIONS

NovoPen® 3, Dial-A-Dose Insulin Delivery System, Novo Nordisk Pharmaceuticals, Inc., 1998.
Merriam-Webster.com Dictionary, Merriam Webster, "Ring", 2020, retrieved on 2020. 4. 13., URL: https://www.merriam-webster.com/dictionary/ring.

* cited by examiner

HOUSING FOR A MEDICAL INJECTION DEVICE

CROSS-REFERENCE TO RELATED APPLICATIONS

This application is a Divisional of U.S. patent application Ser. No. 15/578,326, filed Nov. 30, 2017, which is a 35 U.S.C. § 371 National Stage application of International Application PCT/EP2016/062039 (published as WO 2016/193157), filed May 27, 2016, which claims priority to European Patent Application 15170130.7, filed Jun. 1, 2015; the contents of which are incorporated herein by reference.

THE TECHNICAL FIELD OF THE INVENTION

The invention relates to an injection device for injecting set doses of a liquid drug and more precisely to such injection device comprising a housing moulded from a polymeric material. The invention especially refers to such housing produced by an over-moulding method such as 2K moulding. The invention further relates to a method for moulding such housing using a 2K injection moulding technique.

DESCRIPTION OF RELATED ART

An injection device usually has a housing storing a cartridge containing the liquid drug to be injected. The liquid drug is pressed out from the cartridge through an injection needle by moving a plunger forward inside the cartridge. This forward movement is usually done by a piston rod abutting the plunger which piston rod is moved axially forward by a drive mechanism. The housing is usually made from one or more polymeric components which are usually injection moulded.

An example of such injection device is disclosed in WO 99/38554 (reference is especially made to the FIGS. 15-17, which depicts an injection pen currently sold by Novo Nordisk A/S under the trade name Flexpen®). The proximal housing component is internally provided with a thread which guides a scale drum. The scale drum has a corresponding thread such that the scale drum moves helically out from the housing during rotation. Indicia indicating the various doses a user can select are printed on the scale drum and moves past a window in the housing during rotation. Usually a pointer pointing to the relevant indicia is printed on an external surface of the housing. However, the moulding of internal threads is rather complicated and moulding always involves certain tolerances. Further, the printing process also has tolerances. As a result of these tolerances a number of injection devices are missing a correct alignment between the indicia on the scale drum and the pointer printed on the housing.

A further example of an injection device is provided in WO2001/95959 which discloses an injection device in which the scale drum is provided with threads on the inside and rotatably guided on a threaded tower erected inside the housing. However, also in this injected device, the pointer is printed on the housing in a separate printing process.

A further scale drum configuration is disclosed in WO 2015/197629. Here the scale drum also has an internal thread but this thread is guided on the threaded piston rod which is rotationally locked during dose setting such that the scale drum moves helically both in relation to the piston rod and to the housing during dose setting.

EP 1,819,382 discloses an injection device in which the force for expelling the set dose is delivered by a torsion spring. In such injection device the scale drum is usually restricted to only rotate helically within the boundaries of the housing i.e. the scale drum does not protrude out from the housing. The housing is on the inside provided with an inwardly pointing projection which stops the helical movement of the scale drum in a predetermined position, usually the zero position or the maximum dose setting position. This stop projection can either stop the axial movement of the scale drum as is known from a standard nut and bolt, or it can be a rotational stop which stops the helical movement of the scale drum.

In EP 1,603,610 the thread in the housing guiding the scale drum is formed only as a segment of a thread, however, the pointer is still printed on the housing.

An example of a moulding method in which a first part is moulded where after a second part is moulded over the first part is disclosed in US 2005/0241112. Here an indicator element for a polymeric knob is moulded separately in a first cavity where after it is placed in a second cavity. This is followed by a second mould performed into the second cavity to partly cover the indicator element. This technique is commonly recognized as insert moulding. A similar method for insert moulding of a housing for an injection device is disclosed in U.S. Pat. No. 8,652,387.

2K moulding is also often referred to as multicomponent moulding or over-moulding. In one aspect of 2K moulding a pre-formed element is physically located in the cavity before the last moulding shot is delivered, this is often referred to as insert moulding. In another aspect of 2K injection moulding, the first part and the second part are moulded either in the same cavity through different injections points in a sequential process, or in different cavities also through different injections points and in a sequential process. Generally, in 2K moulding; two different injection moulding units are used to mould the finished product and the second mould is performed before the first mould is cooled such that the two parts or layers are adhered to each other to form a "sandwich" structure.

A process for 2K moulding using a turnable middle section is disclosed in WO 2000/073040. In this process the inner part is first moulded on a core or mandrel which is there after rotated into a second position in which second position the outer part is moulded over the inner part using a second cavity. The first mould is maintained on the same core in both moulding sequences and the fully moulded 2K part is removed from the core after the second mould is performed.

DESCRIPTION OF THE INVENTION

It is thus an object of the present invention to provide an injection device having an improved housing in which the correlation between the indicia on the scale drum and the indicator on the housing is improved.

It is further an object of the invention to fully avoid a relatively expensive printing process while maintaining a high degree of contrast between the housing and the pointer.

The invention is defined in claim 1. Accordingly in one aspect the present invention relates to an injection device comprising a polymeric moulded housing. Internally the polymeric housing accommodates or supports a rotatable scale drum which has an interface structure for guiding the rotatable scale drum helically relatively to the polymeric housing at least during dose setting.

The interface structure on the scale drum can be any structure which can be guided by a thread or even by a part of a thread to introduce a helical movement to the scale drum. In one example the interface structure is a thread provided on an outer surface of the scale drum for guiding the rotatable scale drum helically in relation to the housing. In an alternative, the interface structure can be a thread structure provided on an inside surface of the scale drum. This inner thread structure can be guided on a tower located inside the housing or it can be guided directly on the threaded piston rod which is then maintained rotatably stationary during dose setting.

The housing is internally provided with one or more projections for engaging the rotatable scale drum. The projection can in one example be a thread structure cooperating with the interface structure of the scale drum to guide the scale drum helically or it can be a simple stop projection for stopping the helical movement of the scale drum e.g. in a zero position. Further, any number of projections can be provided e.g. in a combination of a thread projection and a stop projection. The housing also carries a pointer pointing to indicia on the scale drum is provided.

Accordingly at least three different embodiments can be envisaged. In the first embodiment, the interface structure on the scale drum is formed as an external thread and the projection is formed as a thread structure provided on the inner surface of the housing. In the second embodiment, the interface structure is formed as a thread on the inner surface of the scale drum engaging and the projection is formed as an outwardly pointing thread structure provided on a tower forming part of the housing. In the third embodiment the interface means is an internal thread formed inside the scale drum and engaging directly on the piston rod and the projection provided engages the scale drum either axially or rotationally to stop helical movement of the scale drum. Such stop projections could also be provided in the first and the second embodiments.

By thread or thread structure is meant any kind of female or male thread or part of thread that can introduce a helical movement. In the simplest form one part can be a helical thread and the other part just a protrusion engaging the helical thread to introduce a helical movement.

According to the invention, the polymeric housing of the injection device comprises the following two parts:
  a moulded outer housing element, and
  a moulded elongated tubular inner housing element carrying both the pointer and the projection engaging the scale drum.

The outer housing element is moulded over the elongated tubular inner housing element to form one single component referred to as the housing. The elongated tubular inner housing element is moulded prior to moulding the outer housing element and is preferably moulded either in another cavity or in the same cavity using a 2K moulding technique. The moulding is preferably performed on a core or mandrel.

By elongated is meant that the axial or longitudinal length of the inner housing element is longer than the diameter of the element itself. Further, by the term tubular is meant that the element is oblong and hollow as tubes generally are. Since tubes are usually hollow, this implies that the elongated tubular inner housing element has a closed circumference, however, a less than 360 degrees circumference is also possible within the scope of the present invention. By tubular and elongated is not meant any limitation to the actual cross section of the elongated tubular element of the invention.

The elongated tubular inner housing element is formed as one unitary element carrying both the pointer and the projection engaging the scale drum and the position of the projection and the pointer are predetermined and interrelated. In this way the correlation between the pointer and the indicia on the scale drum can be optimized since the alignment between the pointer and the projection engaging the scale drum can be set more accurate. The narrow connection between the pointer and the scale drum (via the projection) will ensure a more precise link between the pointer and the scale drum indicia.

The projection protrudes inwardly from an inner surface of the elongated tubular element and the pointer protrudes outwardly from an outer surface of the elongated tubular inner housing element. The outer housing is moulded over the elongated tubular inner housing element leaving at least a part, and preferably an outer surface part, of the protruding pointer visible for user.

The inner housing element and the outer housing element are in one embodiment moulded from materials which has different visible appearances. The difference in appearances can be provided by a difference in colours or a difference in texture and thus makes the presence of the pointer very visible to the user.

In one aspect the one or more projection is a thread engaging the interface structure of the scale drum for guiding the rotation of the scale drum. However, the projection could also be a stop means for stopping the rotation of the scale drum in a predetermined position. Such position would usually be the zero position or the maximum dose setting position or both positions. It is thus equally important to correlate the indicia with the stop means in order to have the pointer to point to the correct indicia in the stop position The scale drum can be the type in which the helical groove is provided on the outer surface of the scale drum such that the scale drum is guided in a thread in the housing pointing towards the centre line of the pen-shaped injection device. Alternatively, the scale drum is provided with threads on its inside, in which case the scale drum is rotatable guided on a tower erected inside the housing of the injection device. This tower would then carry the thread which then points away from the centre line of the pen-shaped injection device. In the latter case, the erected tower can be integrally formed in the 2K moulding process.

In an alternative solution for an injection device as disclosed in WO 2015/197629 the interface structure on the scale drum can be helically guided by the outer thread provided on the piston rod. In this case the piston rod is rotationally maintained in locked position relatively to the housing at least during dose setting such that the scale drum moves helically relatively to the housing during dose setting.

The moulded outer housing element comprises a window, e.g. formed as a radial opening in the outer housing element and the pointer preferably points towards this window thereby indicating the set dose size for the user. The protruding pointer preferably makes up a part of the window frame and directly abuts with the scale drum, such that no element is present between the visible part of the protruding pointer and the scale drum. A user is then able to view the indicia on the scale drum through the window and the pointer points directly to the relevant indicia. The window could further be covered by a transparent glassing e.g. made from a transparent polymeric material, through which the user can inspect the indicia on the scale drum. Such transparent element can in one example be insert moulded to the housing i.e. the transparent element is located in the cavity before the polymeric material is injected into the cavity.

However, the pointer can also penetrate through the outer housing element in a position axially retracted from the window, the important feature being that the projection and the pointer is moulded on the same element and in the same process to thereby maximise the correlation between the indicia on the scale drum and the position of the pointer. Further, a difference in the visible appearance of the two housing elements provides a very visible pointer.

In one aspect, the elongated tubular inner housing element covers the window in the outer housing element in which case the elongated tubular inner housing element needs to be provided with a window aligned with the window of the outer housing element thus allowing the user to visually inspect the indicia representing the set dose size. However, the elongated tubular inner housing element need not be formed to cover the window of the outer housing element, the longitudinal distance in which the two parts cover each other can be located out of the range of the window.

The elongated tubular inner housing element is preferably formed as a cylindrical element. By cylindrical is meant that the individual lines forming the outer surface run in parallel. The cross-section can thus be any kind of a polygonal configuration. However, a circular cross-section is preferred for pen-shaped injection devices, In one aspect of the invention, the elongated tubular inner housing element extends outside the axial parameter of the outer housing element. This is very beneficial since the so extending part of the elongated tubular inner housing element can be used for securing other elements such as a dose dial button. Further, when 2K moulding the housing, the same core or mandrel can be used for the two different cavities used in the moulding process. The elongated tubular element is first moulded on the core or mandrel which is there after revolved to the second cavity thus moulding the outer housing element directly on the elongated tubular element where after the finished housing is cooled and removed from the core or mandrel.

In order to simplify the moulding process, the thread is preferably formed as one or more segments of a thread. Such segments are preferably less than one single sweep i.e. less than 360 degrees. This greatly simplifies the removal of the finished housing from the core or mandrel after the second mould has been cooled.

When only very angular small segments are used it can be beneficial to provided more than one segment in the axial direction. Especially if the scale drum is short but travels a long distance. In such case a plurality of longitudinal separated thread segments are required in order to maintain contact with the interface structure of the scale drum as it travels axially.

In the aspect in which the projection is formed as a stop means for stopping helical movement of the scale drum, the stop can be an axial stop which engages the scale drum to stop in a predetermined axial position. Such axial stop would thus abut the scale drum at a distal or at a proximal surface of the scale drum.

In a further embodiment, the scale drum can be provided with a stop surface provided in a circumferential and rotational plane and the stop means could thus abut such stop surface to stop further rotational movement of the scale drum.

It is also possible to provide the elongated tubular element with both a thread and a stop means.

The upper surface of the pointer is usually aligned with the outer surface of the outer housing element to form a smooth outer surface of the injection device. Further, the inner surface of the pointer is aligned with the inner surface of the elongated tubular inner housing element to also form a smooth interior surface against which the scale drum slides.

The elongated tubular inner housing element and especially the pointer is preferably optical different from the outer surface of the outer housing element such that a user can quickly identify which part is the pointer and which part is the housing. In order to further enhance the contrast, the outer housing element and the elongated tubular inner housing element can be moulded from different polymeric materials and/or have different colours.

The finished housing is usually the outer shell of an injection device; however, the housing could also form only part of the outer shell e.g. by being attached to a cartridge-holder carrying the cartridge containing the liquid drug. In an alternative the moulded housing can be surrounded by a thin metal sheet which is then the outer shell.

The scale drum can be any kind of rotatable and axially moving scale drum, the scale drum is preferably provided with a helical groove or thread such that the resulting movement is helically as explained. In WO 99/38554, the scale drum rotates out from the housing during dose setting. However, in the new generation of spring-driven automatic injection devices as e.g. known from EP 1,819,382, the scale drum moves within the boundaries of the housing both during dose setting and during dose ejection. The latter is also the case for the injection device disclosed in WO 2015/197629.

The present invention further relates to a method for moulding the polymeric housing of the injection device. The method comprises the steps of:
  (i) moulding an elongated tubular inner housing element having an outer surface carrying a pointer and an inner surface carrying a projection, and
  (ii) moulding an outer housing element over the elongated tubular element leaving at least a part of the pointer visible.

The elongated tubular inner housing element is moulded prior to moulding the outer housing element and the outer housing element and the elongated tubular inner housing element are preferably but not necessarily moulded from different polymeric materials. A preferred moulding technique is 2K moulding in which the elongated tubular inner housing element is first moulded where after the outer housing element is moulded over the tubular element preferably using two different cavities but maintaining the housing, or actually the elongated tubular element, on the same core or mandrel as disclosed in WO 2000/073040.

Further, in one aspect, the outer housing element and the elongated tubular inner housing element have different colours or different physical texture to thereby enhance the visual appearance of the pointer.

The present invention thus relate to a medical injection device and preferably to a pen-shaped injection device. The housing of the injection pen preferably has an oblong shape and a circular cross-section and the outer housing element can either form the housing in its entirety or the outer housing element can form a part of a larger housing. The injection pen can either be a pre-filled injection device or a durable injection device and in either case it can be a manual driven injection pen or an automatic injection pen.

Definations

An "injection pen" is typically an injection apparatus having an oblong or elongated shape somewhat like a fountain pen for writing. Although such pens usually have a circular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing.

"Cartridge" is the term used to describe the container containing the drug. Cartridges are usually made from glass but could also be moulded from any suitable polymer.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button e.g. provided at the proximal end of the injection device to release—fully or partially—the force accumulated in the spring when carrying out the injection.

Further the term "injection needle" defines a piercing member adapted to penetrate the skin of a subject for the purpose of delivering or removing a liquid. For many pen systems, the needle cannula of the injection needle comprises a front part for penetrating the skin of the user and a back part for penetrating the septum of the cartridge thus creating a liquid flow between the interior of the cartridge and the subcutaneous layer of the user.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the housing element to which the cartridge-holder is attached, whereas the term "proximal end" is meant to refer to the opposite end pointing away from the cartridge-holder and usually carrying the dose dial button. Distal and proximal is meant to be along an axial orientation extending along the longitudinal axis of the injection device and is further indicated in the figures.

Figure 1:
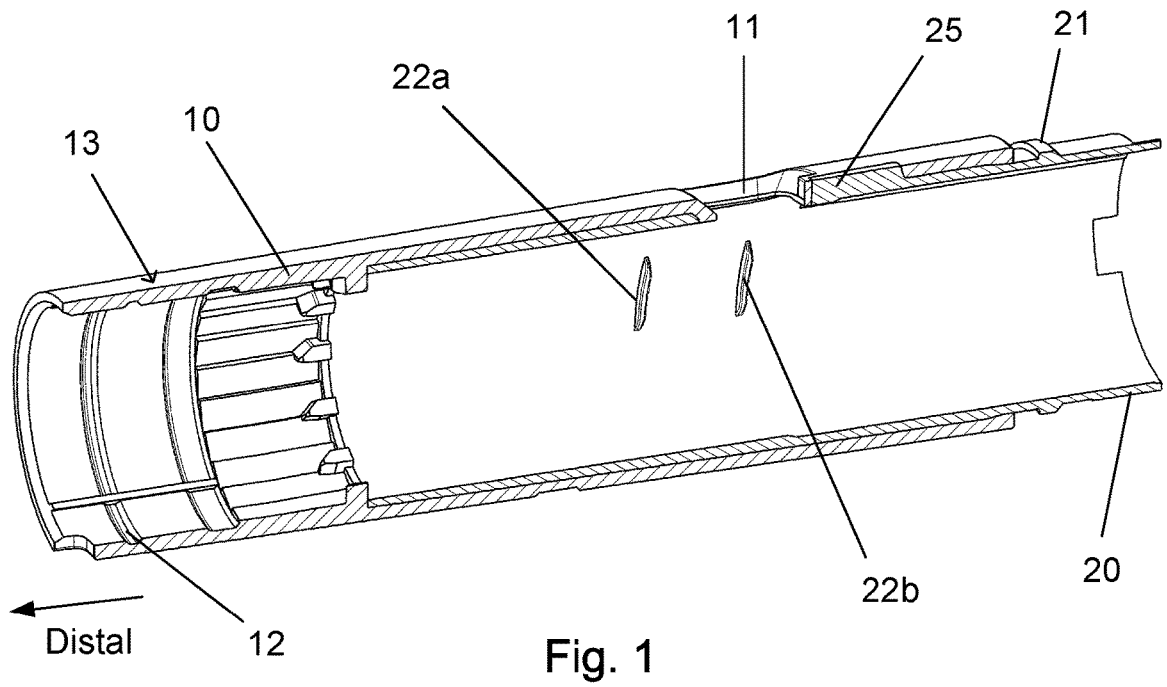
FIG. 1 show a cut-open view of the housing according to the invention.

In FIG. 1 the outer housing element from the second mould is numbered "10" and the inner housing element from the first mould is numbered "20".

The outer housing element 10 is moulded over the inner housing element 20 and comprises a window 11 through which a user can view a non-shown scale drum 15. As can be seen in FIG. 1, the inner housing element 20 extends out from the outer housing element 10 in a longitudinal direction.

The extended part of the inner housing element 20 is provided with a circular ridge 21 which rotatable secures a non-shown dose dial button. The distal end of the outer housing element 10 is provided with an internal groove 12 securing a non-shown cartridge-holder which again supports a non-shown cartridge containing the liquid drug. Together the outer housing element 10 and the cartridge-holder make up the body of an injection device which e.g. could be a pre-filled injection device i.e. an injection device wherein the cartridge-holder is permanently and irreversible secured to the housing 10.

The term body is herein used to define the entire outer boundaries of the injection device. However, in the following, the term housing is meant to imply either the full body if the body is moulded as one single element or the term housing can imply only a part of the full body if the body is made from a plurality of elements e.g. a housing part and a cartridge holder.

When setting a dose, the user rotates the non-shown dose setting button which causes the scale drum 15 to rotate. The scale drum 15 is disclosed in FIG. 4 and is in the depicted embodiment externally provided with a helical groove or thread 16 which is guided on a thread 22 preferably formed from a plurality of thread segments 22a-c such that the scale drum 15 move in a helical movement whereby indicia printed in a helical row on the outer surface of the scale drum 15 pass by the window 11 in the outer housing element 10 thus indicating the size of the set dose.

The thread 22 formed in the inner housing element 20 can be a full thread 22 i.e. having more than a 360 degree sweep, or the thread 22 can be made from one or more thread segments 22a-c as long as the inner housing element 20 is formed as one unitary element carrying both the thread 22 or the thread segments 22a-c and a pointer 25.

In a non-shown embodiment the thread 16 can be located internally in the scale drum 15 and the housing provided with a tower on which the scale drum 15 is helically moved. In such embodiment, the thread segments 22a-b points outwardly. Further, the non-shown internal thread can be guided on the outer thread of a piston rod.

All though the figures disclose a plurality of thread segments 22a-c only one such segment 22a-c is actually needed. However in order to properly guide a short scale drum 15 over a large distance a plurality of thread segments 22a-c are suggested. These segments 22a-c should be provided axially displaced in an axial distance depending on the length of the scale drum 15. As an alternative to thread segments 22a-c a full thread 22 can be used, but for moulding purposes the sweep of the thread 22 should be less than 360 degrees, in which case a plurality of such sweeps could be provided.

Figure 2:
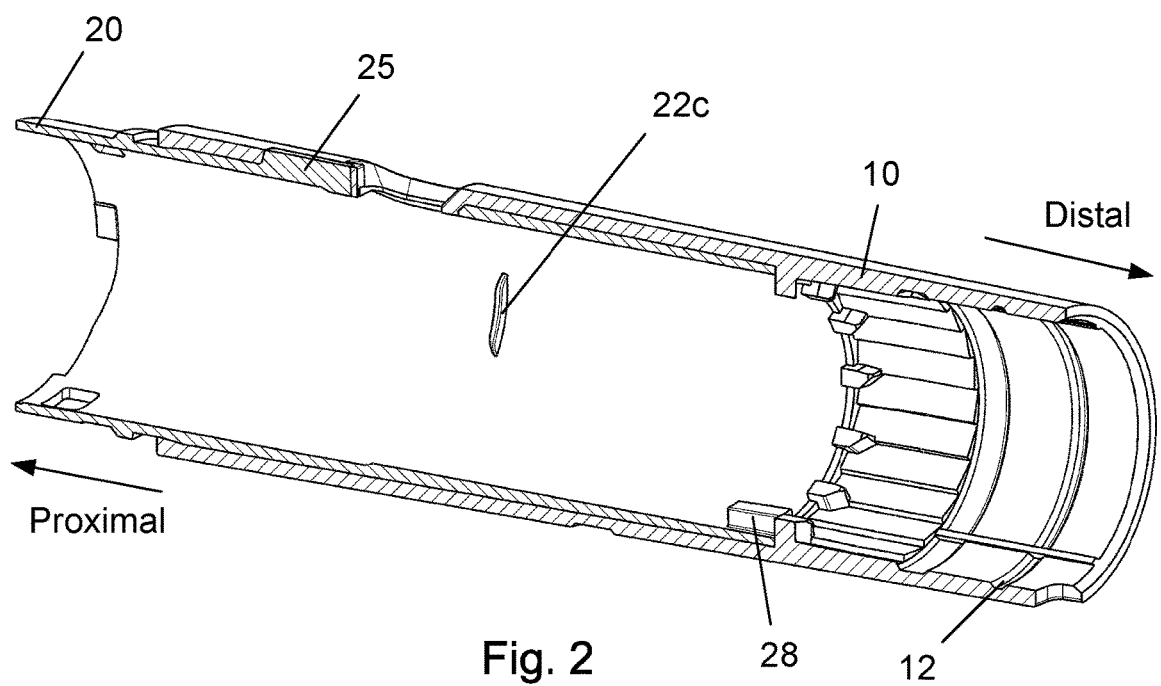
FIG. 2 show the cut-open housing according to FIG. 1 viewed from a different angle.

FIGS. 1 and 2 further discloses that all the thread segments 22a-c and the pointer 25 form integral parts of the inner housing element 20. The outer housing element 10 has an outer surface 13 which is to be held in the hand of the user during operation of the injection device. Further, the inner housing element 20 carrying the thread segments 22a-c and the pointer 25 can also be provided with a stop 28 which will be explained later.

Figure 3:
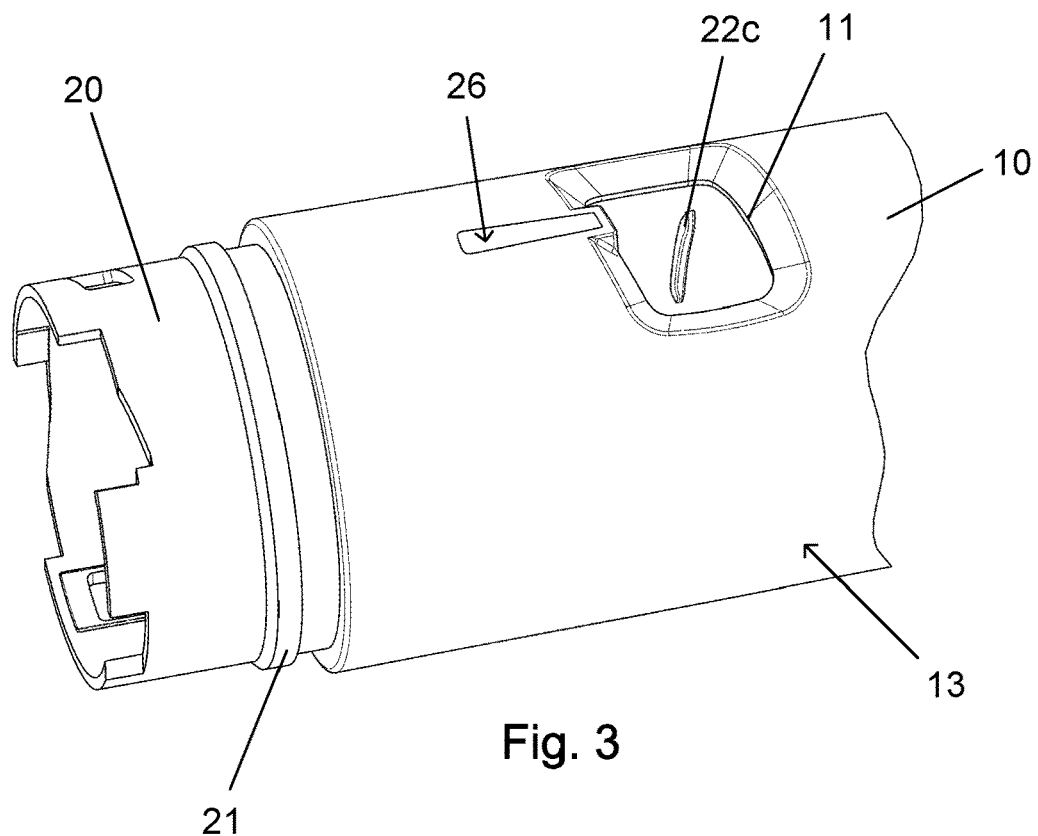
FIG. 3 show a perspective view of the proximal end of the housing.

FIG. 3 discloses an enlarged view of the proximal end of the housing which will be explained later.

Figure 4:
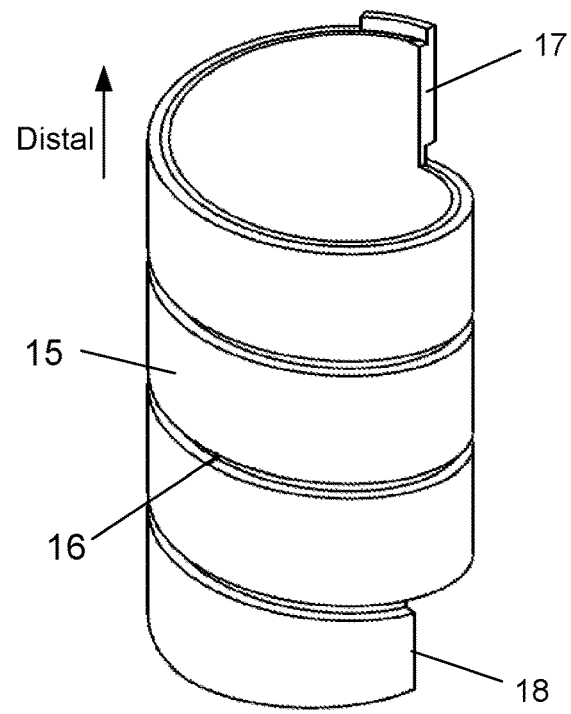
FIG. 4 show a perspective view of the scale drum.

FIG. 4 discloses the scale drum 15 which is helically guided in the thread segments 22a-c. Such scale drum 15 is well known in the art and is externally provided with indicia viewable through the window 11. The scale drum 15 is distally provided with a stop surface 17 which lies in the circumferential and rotational plane. A similar proximal stop surface 18 is further provided. In the end position one of these stop surfaces 17, 18 abut the stop 28 provided in the tubular element 10. This stop position is either the zero position or the maximum dose setting position. A further stop can be provided in a different not-shown element which is coupled to the proximal end of the tubular element 10 such that the scale drum 15 strikes both a zero stop and a maximum stop. The individual position of these two stops would depend on the angle of the thread segments 22a-c, i.e. depend upon which way the scale drum 15 rotates during dose setting.

By having the stop 28 moulded in the same mould as the pointer 25 a very precise correlation between the stop position and the indicia on the scale drum 15 can be obtained.

The stop 28 provided on the inner housing element 20 does not explicit require the thread segments 22a-c to also be formed in the inner housing element 20. A solution in which the stop 28 and the pointer 25 are provided on the inner housing element 20 and the thread segments 22a-c are provided in the outer housing element 10 can also be envisaged.

Further, if the scale drum 15 is guided directly on the outer thread a the piston rod, only stop projections 28 are required.

Figure 5:
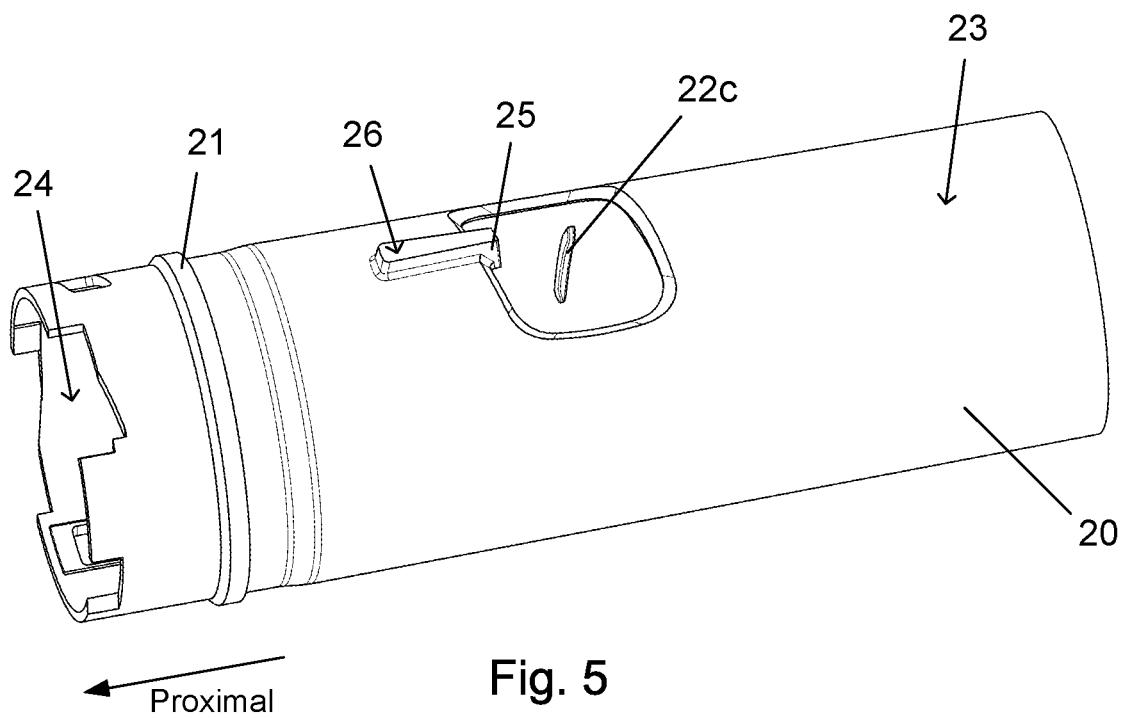
FIG. 5 show a perspective view of the inner housing element.
Figure 6:
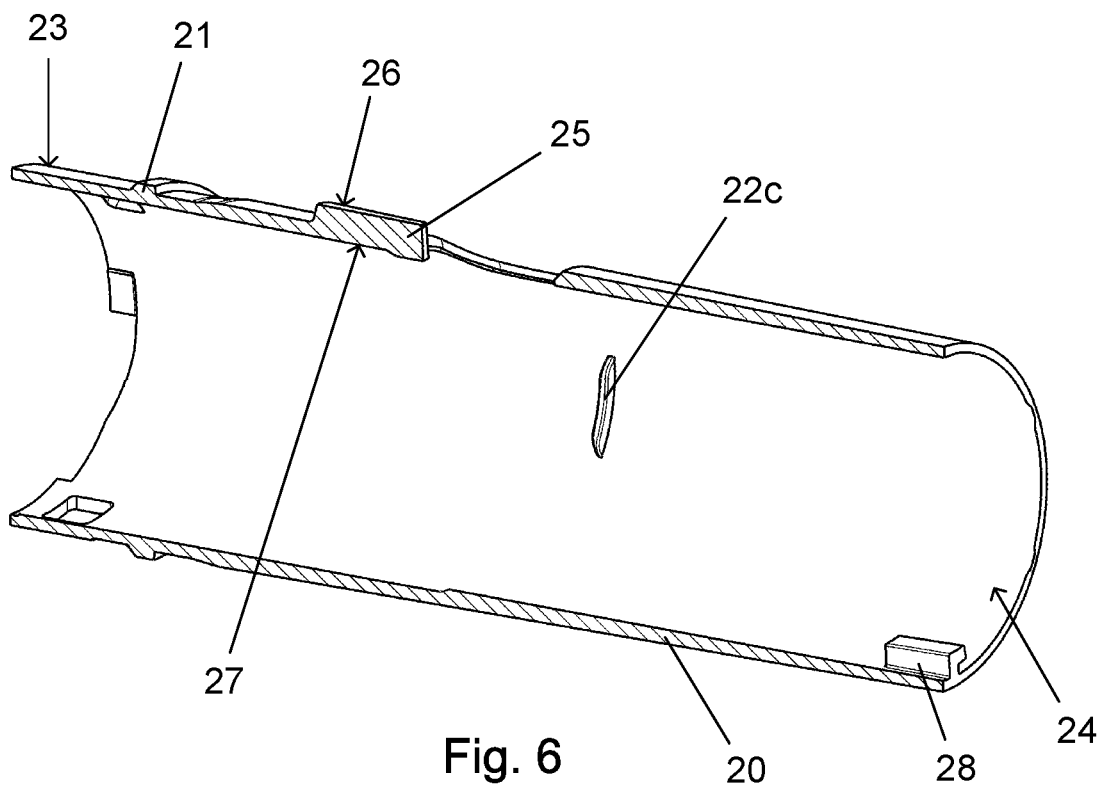
FIG. 6 show a cross sectional view of the inner housing element of FIG. 5.

FIGS. 5 and 6 disclose the inner housing element 20 before the outer housing element 10 is moulded. The inner housing element 20 has an outer surface 23 and an inner surface 24 (surfaces are indicated by arrows). Further, the pointer 25 has an outer surface 26 and an inner surface 27.

The inner surface 27 of the pointer 25 is preferably aligned with the inner surface 24 of the inner housing element 20 as disclosed in FIG. 6.

As seen in FIG. 5 and FIG. 6, the pointer 25 protrude a distance above the outer surface 23 of the inner housing element 20, a distance that makes the outer surface 26 of the pointer 25 to be aligned with the outer surface 13 of the outer housing element 10. Further, the thread segments 22a-c protrudes beyond the inner surface 24 of the inner housing element 20 thus making it possible for the thread segments 22a-c to engage the female part of the thread 16 in the scale drum 15 carrying the indicia indicating the size of the set dose.

In production, the inner housing element 20 is first moulded on a core or mandrel in a first cavity where after, the core or mandrel still carrying the inner housing element 20 is moved e.g. by rotation, to a second cavity in which the outer housing element 10 is moulded over the inner housing element 20. The two cavities used are preferably feed from two different injection moulding machines as is common when over-moulding (2K moulding). After moulding the housing is removed from the core or mandrel after proper cooling.

The inner housing element 20 which is moulded first in one operation thus has the pointer 25 and the thread segments 22a-c in an interrelated and predetermined position which means that the scale drum 15 can be very precisely guided such that an exact and prober alignment between the indicia on the scale drum 15 and the position of the pointer 25 can be established.

Further, a clear difference in the visible appearance of the pointer 25 and the outer housing element 10 can be obtained e.g. by using different textures in the two mouldings or by using different colours of polymers in the moulding process. It is also possible to add a lubricant to the polymer when moulding the inner housing element 20 which would then lower the friction between the thread segments 22a-c and the scale drum 15.

In FIG. 3 it is disclosed that the outer surface 26 of the pointer 25 radially is aligned with the outer surface 13 of the outer housing element 10 thus all together forming a smooth outer surface. In the disclosed embodiment the pointer 25 is axially removed a small distance from the window 11, however, the pointer 25 can in another embodiment form part of the window frame such that the part of the pointer 25 integrated in the window frame directly abuts the scale drum 15.

Some preferred embodiments have been shown in the foregoing, but it should be stressed that the invention is not limited to these, but may be embodied in other ways within the subject matter defined in the following claims.

The invention claimed is:

1. An injection device for injecting set doses of a liquid drug, comprising:
    a pen-shaped polymeric housing having one or more thread segment projections and internally accommodating a rotatable scale drum wherein the rotatable scale drum has a helical groove for guiding the rotatable scale drum helically relatively to the polymeric housing and wherein the rotatable scale drum carries a plurality of indicia viewable through a window provided in the polymeric housing, and
    a pointer pointing to an indicia thereby indicating the size of the set dose, and the polymeric housing comprises:
        a moulded outer housing element having an outer surface, and
        a moulded elongated tubular inner housing element having an inner portion and an outer portion, wherein the elongated tubular inner housing element carries both the pointer for indicating the size of a set dose and the one or more thread segment projections for engaging the rotatable scale drum,
    wherein the elongated tubular inner housing element comprises an inner portion surface from which the one or more thread segment projection protrude inwardly for engaging the rotatable scale drum and an outer portion surface from which the pointer protrudes outwardly,
    wherein the moulded outer housing element is injection moulded over the elongated tubular inner housing element to form one single component leaving at least a part of the outer portion protruding pointer visible, and
    wherein the outer housing element and the elongated tubular inner housing element have different visible appearances such that the pointer is optically different from the outer surface of the outer housing element.

2. An injection device according to claim 1, wherein the one or more thread segment projections is a thread engaging the helical groove of the rotatable scale drum.

3. An injection device according to claim 2, wherein the one or more thread segment projections is formed as one or more segments.

4. An injection device according to claim 3, wherein the one or more segments are provided in different longitudinal positions.

5. An injection device according to claim 1, wherein the thread segment projections are a stop structure abutting a surface on the scale drum in a stop position.

6. An injection device according to claim 1, wherein the elongated tubular inner housing element extends out from the outer housing element in at least one longitudinal direction such that at least a part of the elongated tubular inner housing element constitutes an extension of the outer housing element.

7. An injection device according to claim 1, wherein an outer surface of the pointer is aligned with the outer surface of the outer housing element.

8. An injection device according to claim 1, wherein the pointer forms part of the window.

9. An injection device according to claim 1, wherein the outer housing element and the elongated tubular inner housing element are moulded from different polymeric materials.

10. An injection device according to claim 1, wherein the outer housing element and the elongated tubular inner housing element are moulded from polymeric materials having different visual appearances.

* * * * *